United States Patent
Mace et al.

(10) Patent No.: US 6,600,086 B1
(45) Date of Patent: Jul. 29, 2003

(54) BREATHABLE DIAPER OUTER COVER WITH FOAM DAMPNESS INHIBITOR

(75) Inventors: Tamara Lee Mace, Doraville, GA (US); Ann Louise McCormack, Cumming, GA (US); Carol Ann Blaney, Roswell, GA (US); Audrie Tomoko Ono, Atlanta, GA (US); Michael Tod Morman, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 357 days.

(21) Appl. No.: 09/584,643

(22) Filed: May 31, 2000

(51) Int. Cl.$^7$ .................................. A61F 13/15
(52) U.S. Cl. ................ 604/369; 604/378; 604/385.101
(58) Field of Search ........................ 604/367, 369, 604/378, 385.101, 385.01

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,308,303 A | * 12/1981 | Mastroianni et al. | 428/90 |
| 4,340,563 A | 7/1982 | Appel et al. | 264/518 |
| 4,394,930 A | * 7/1983 | Korpman | 220/444 |
| 4,663,220 A | 5/1987 | Wisneski et al. | 428/221 |
| 4,704,116 A | 11/1987 | Enloe | 604/385 A |
| 4,940,464 A | 7/1990 | Van Gompel et al. | 604/396 |
| 5,046,272 A | 9/1991 | Vogt et al. | 38/143 |
| 5,104,116 A | 4/1992 | Pohjola | 271/185 |
| 5,224,405 A | 7/1993 | Pohjola | 83/24 |
| 5,226,992 A | 7/1993 | Morman | 156/62.4 |
| 5,817,081 A | 10/1998 | LaVon et al. | 604/378 |
| 6,152,906 A | * 11/2000 | Faulks et al. | 604/385.01 |

FOREIGN PATENT DOCUMENTS

| | | | |
|---|---|---|---|
| EP | 0 217 032 | 4/1987 | D04H/13/00 |
| WO | 97/36561 | 10/1997 | |
| WO | 00/10497 | 3/2000 | |

* cited by examiner

Primary Examiner—Weilun Lo
Assistant Examiner—Michael Bogart
(74) Attorney, Agent, or Firm—Pauley Petersen Kinne & Erickson

(57) ABSTRACT

An absorbent article including a liquid-permeable bodyside liner, an absorbent core layer and a breathable outer cover is provided with a hydrophobic foam dampness-inhibiting layer between the absorbent core and the outer cover. The hydrophobic foam dampness-inhibiting layer maintains an air space within the foam. The air space acts as a thermal insulator, dampness-perception inhibitor and moisture passageway. The resulting product is an absorbent garment having a breathable outer cover material with reduced perception of dampness on the outer surface of the outer cover.

21 Claims, 11 Drawing Sheets

BREATHABLE DIAPER OUTER COVER WITH FOAM DAMPNESS INHIBITOR

FIELD OF THE INVENTION

The present invention is directed to an absorbent product having at least a top layer, an absorbent core, and a breathable outer cover. A hydrophobic foam dampness-inhibiting layer is disposed directly beneath the breathable outer cover, thereby maintaining an air space within the foam layer. The air space causes a reduction in perceived surface dampness on the outer surface of the breathable outer cover when the absorbent core is wet.

BACKGROUND OF THE INVENTION

Absorbent articles, such as diapers, child training pants, adult incontinence garments, swim wear and the like, typically include at least a liquid-permeable top layer for direct contact with the wearer, an absorbent core layer, and a substantially liquid-impermeable outer cover. The absorbent core is positioned between the top layer and the outer cover. When the absorbent article is exposed to a liquid insult, liquid passes through the top layer and into the absorbent core. The outer cover prevents the liquid in the absorbent core from leaving the garment.

Many of today's absorbent garments utilize breathable outer cover materials. Breathable outer cover materials are substantially impermeable to liquids, but are permeable to water vapor. Breathable outer cover materials permit escape of water vapor from the absorbent garment, increasing the garment comfort and reducing skin rashes and other irritations that result when water vapor is maintained inside the garment and heated by the wearer's body. Many of today's absorbent garments are highly breathable, for maximum wearer comfort.

One shortcoming of breathable absorbent articles is a cold, damp, clammy feel that often occurs on the outside of the garment, i.e., on the outside of the outer cover. As liquid water in the absorbent core evaporates and passes through the microporous outer cover material, the associated evaporative cooling causes a lowering of temperature of the absorbent core and the adjacent outer cover material, resulting in a clammy, damp-feeling outer cover. The high moisture flux through the outer cover also causes the air in the vicinity of the outer cover surface to be at or near saturation. Humid air has a higher thermal conductivity than dry air, which the fingers can sense, further exacerbating perceptions of dampness.

There is thus a need or desire in the absorbent garment industry for absorbent articles which are highly breathable, yet which reduce or avoid the perceived dampness caused by evaporative cooling.

SUMMARY OF THE INVENTION

The present invention is directed to an absorbent article having a breathable outer cover and reduced perceived outer cover dampness. The absorbent article includes at least a liquid-permeable top layer, a breathable, substantially liquid impermeable outer cover, and an absorbent core layer between the top layer and the outer cover. In accordance with the invention, a hydrophobic foam dampness-inhibiting layer is interposed between the absorbent core and the breathable outer cover. This hydrophobic foam layer maintains air within the foam, thereby providing several beneficial functions to the diaper.

One benefit provided by the foam dampness-inhibiting layer is that the air space insulates the absorbent core from the outer cover and slows heat transfer from a person's fingers touching the outer surface of the outer cover to the diaper, causing the diaper to feel less clammy or cold. Another benefit is that the air space in combination with the foam layer provides a resilient, soft, springy surface to the fingers, giving an aesthetic improvement over feeling just wet gel beneath the outer cover in the absence of the foam layer. In theory, the air space also allows pathways for side diffusion and convection, speeding the removal of moisture from the diaper, especially moisture near the skin. This increased removal of moisture contributes to reduced, therefore improved, skin hydration. Furthermore, the air space separates the wet absorbent core of super-absorbent material, gel or pulp, from resting against the inside surface of the outer cover material, thereby allowing for a much greater surface area in which water molecules may migrate across the gel/air interface. Finally, this invention teaches a foam dampness-inhibiting layer that is permeable enough to not occlude moisture from leaving the diaper in any appreciable amount.

With the foregoing in mind, it is a feature and advantage of the invention to provide an absorbent article having a breathable outer cover in combination with a hydrophobic foam dampness-inhibiting layer that slows heat transfer from the fingers touching the outer cover to an absorbent core, thus reducing clamminess and coolness felt at the outer cover compared to prior art absorbent articles.

It is a further feature and advantage of the invention to provide an absorbent garment from which moisture is readily removed, thereby resulting in reduced skin hydration.

It is also a feature and advantage of the invention to provide an absorbent article having a resilient, soft, springy surface feel.

It is also a feature and advantage of the invention to provide diapers, child training pants, adult incontinence garments, swim wear, and other (e.g. medical) absorbent products which embody the features of the improved absorbent article of the invention.

The foregoing and other features and advantages will become further apparent from the following detailed description of the presently preferred embodiments, read in conjunction with the accompanying drawings. The detailed description and drawings are intended to be illustrative rather than limiting, the scope of the invention being defined by the appended claims and equivalents thereof.

DEFINITIONS

Figure 1:
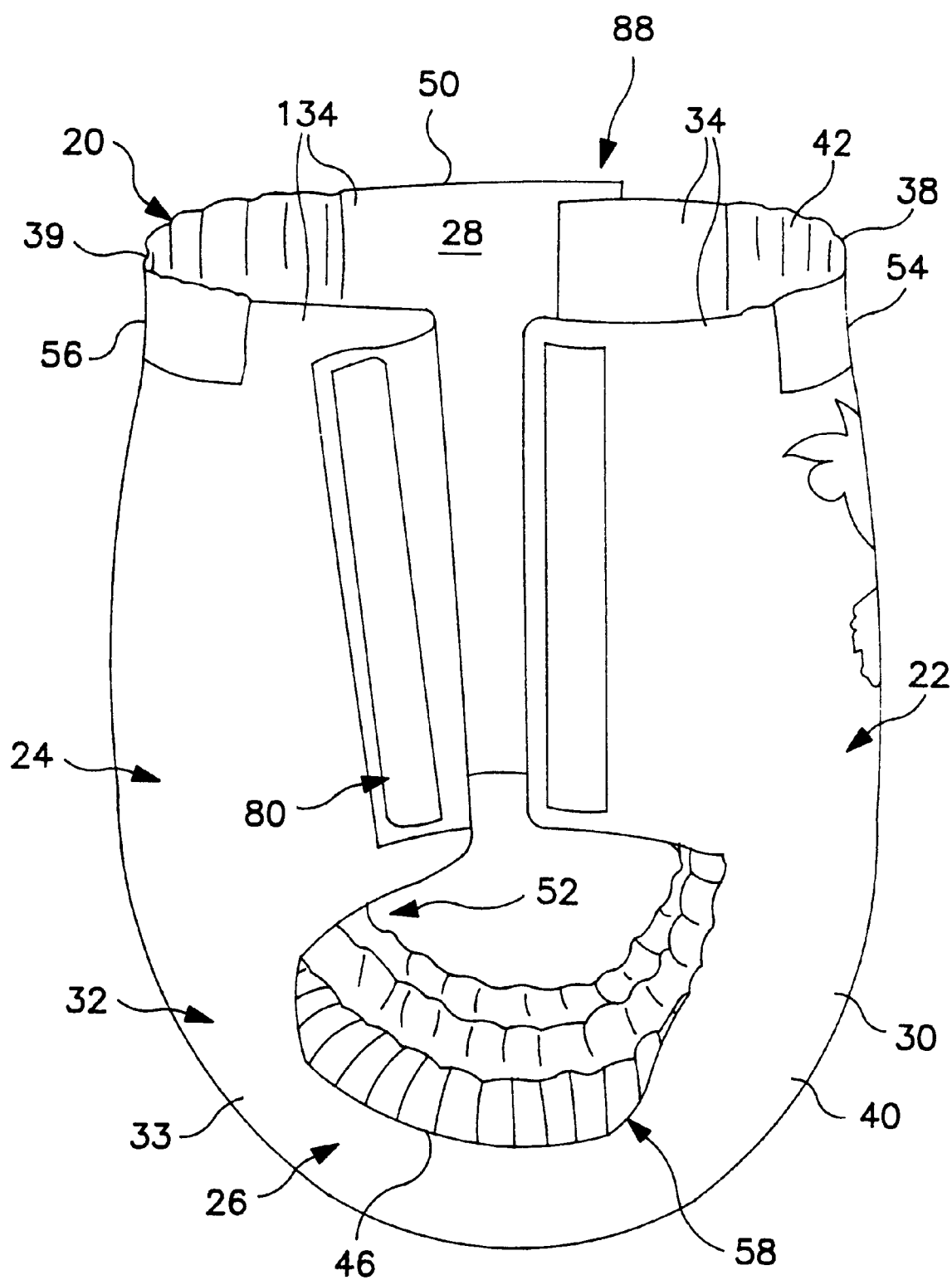
FIG. 1 is a perspective view of an absorbent article of the invention.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

The terms "breathable film," "breathable laminate" or "breathable outer cover material" refer to a film, laminate, or outer cover material having a water vapor transmission rate ("WVTR") of at least about 300 grams/m$^2$24 hours, using the WVTR Test Procedure described herein. Breathable materials typically rely on molecular diffusion of vapor, and are substantially liquid impermeable.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element. "Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Foam material" refers to a material made with the aid of a foaming process. The term "open cell foam material" refers to a foam layer whose cells interconnect, or otherwise create voids from one surface of the layer to the opposite surface. The term "closed cell foam material" refers to a foam layer whose cells are not substantially interconnected.

"Hydrophilic" describes materials or the surfaces of materials which are wetted by the aqueous liquids in contact with the materials.

"Hydrophobic" describes materials or the surfaces of materials which are not wetted by the aqueous liquids in contact with the materials.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or voids between fibers or filaments in a nonwoven web, are large enough and frequent enough to permit leakage and flow of liquid water through the material.

Figure 2:
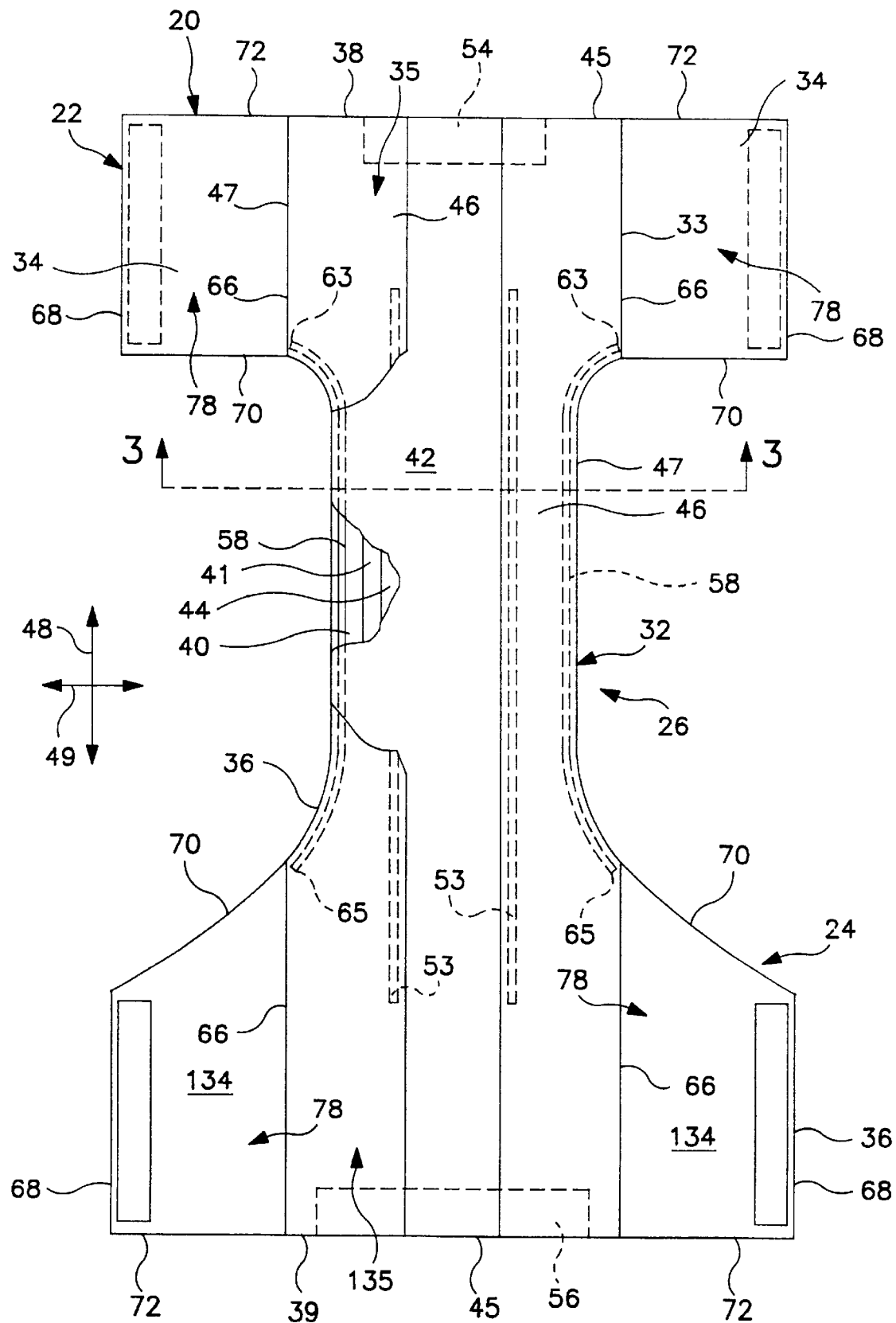
FIG. 2 is a plan view of the absorbent garment of FIG. 1 in a partially disassembled, stretched flat state, showing the surface of the article that faces the wearer when the article is worn, and with portions cut away to show the underlying features.

"Longitudinal" and "transverse" have their customary meaning, as indicated by the longitudinal and transverse axes depicted in FIG. 2. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Microfibers" are small diameter fibers typically having an average fiber denier of about 0.005–10, preferably about 0.05–6, more preferably, about 1–4. Fiber denier is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements ,and the elements being capable of separation without substantial permanent deformation or rupture. The required separation force is typically beyond that encountered while wearing the absorbent garment.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a pant-like absorbent garment having a hydrophobic foam dampness-inhibiting layer between an absorbent core layer and an outer cover. The foam layer, due to its three-dimensional structure, maintains an air space within the foam layer. The air space acts as an insulator, dampness inhibitor and moisture passageway.

The principles of the present invention can be incorporated into any suitable disposable absorbent article. Examples of such suitable articles include diapers, training pants, feminine hygiene products, incontinence products, other personal care or health care garments, or the like. For ease of explanation, the description hereafter will be in terms of a child's training pant.

Referring to FIG. 1, a disposable absorbent article, such as a training pant 20, is illustrated in a partially fastened condition. The training pant 20 includes an absorbent chassis 32. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIG. 2, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent chassis 32 includes a relatively rectangular composite structure 33, a pair of transversely opposed front side panels 34, and a pair of transversely opposed back side panels 134. The composite structure 33 and side panels 34 and 134 may be integrally formed or may include two or more separate elements, as shown in FIGS. 1 and 2. The illustrated composite structure 33 includes multiple layers (described below) including an outer cover 40, a bodyside liner 42 which is connected to the outer cover in a superposed relation, an absorbent core 44 which is located between the outer cover 40 and the bodyside liner 42, a hydrophobic foam dampness-inhibiting layer 41 which is located between the absorbent core 44 and the outer cover 40, and a pair of containment flaps 46. The rectangular composite structure 33 has opposite linear end edges 45 that form portions of the front and back waist edges 38 and 39, and opposite linear side edges 47 that form portions of the side edges 36 of the absorbent chassis 32. Leg openings 52 (FIG. 1) are generally defined by portions of the transversely opposed side edges 36 in the crotch region 26. For reference, arrows 48 and 49 depicting the orientation of the longitudinal axis and the transverse axis, respectively, of the training pant 20 are illustrated in FIG. 2.

With the training pant 20 in the fastened position as partially illustrated in FIG. 1, the front and back waist regions 22 and 24 are joined together to define a three-dimensional pant configuration having a waist opening 50 and a pair of leg openings 52. The front waist region 22 includes the portion of the training pant 20 which, when worn, is positioned on the front of the wearer while the back waist region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front waist region 22 of the absorbent chassis 32 includes the transversely opposed front side panels 34 and a front center panel 35 (FIG. 2) positioned between and interconnecting the side panels. The back waist region 24 of the absorbent chassis 32 includes the transversely opposed back side panels 134 and a back center panel 135 (FIG. 2) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

Figure 3:
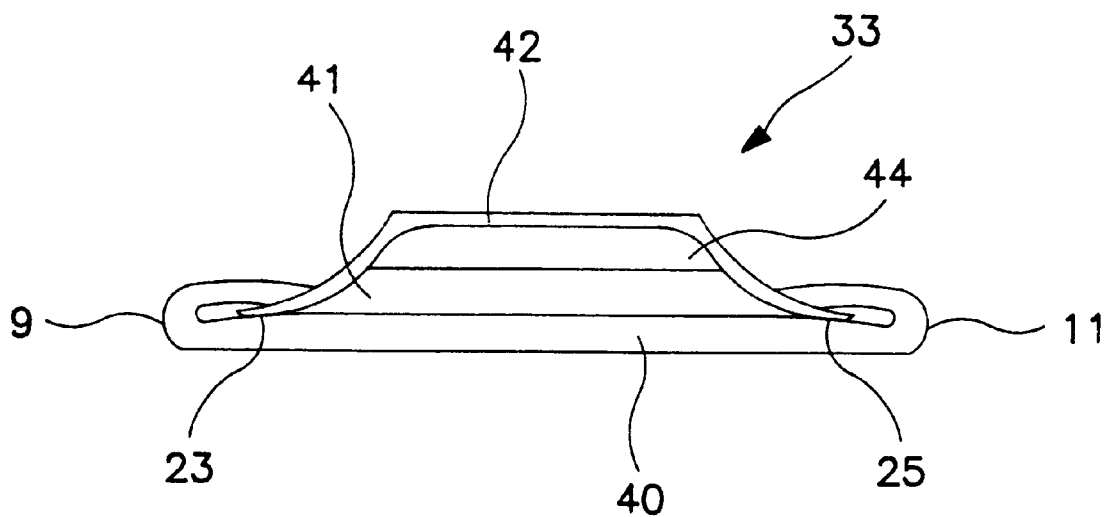
FIG. 3 is an expanded sectional view of an absorbent article of the invention, taken along the line 3—3 in FIG. 2.

The absorbent chassis 32 is configured to contain and/or absorb any body exudates discharged from the wearer. FIG. 3 shows an expanded cutout view of the individual layers of the composite structure 33 in the crotch region 26, taken along line 3—3 in FIG. 2. Referring to FIG. 3, the composite structure 33 includes several layers. As mentioned, the layers include the breathable outer cover 40, the liquid-permeable bodyside liner 42 which is connected to the outer cover in a superposed relation, the absorbent core 44 which is located between the outer cover 40 and the bodyside liner 42, and the hydrophobic foam dampness-inhibiting layer 41 which is located between the absorbent core 44 and the outer cover 40.

In the embodiment shown, the bodyside liner 42 and the outer cover 40 are wider than the absorbent core 44 and the hydrophobic foam dampness-inhibiting layer 41. The bodyside liner 42 substantially surrounds the absorbent core 44 and the hydrophobic foam dampness-inhibiting layer 41 on three sides, and is affixed at end regions 23 and 25 to the outer cover 40 using an adhesive, ultrasonic or thermal bonding technique. The outer cover 40 is folded over at both lateral ends 9 and 11, so that it overlaps and envelops the edges 23 and 25 of the bodyside liner 42. Within the overlap, the layers can be bonded together using thermal, ultrasonic, or adhesive bonding.

As mentioned, the absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 2) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 2). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by thermal lamination or by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made, as described below. While it is not a necessity for the outer layer to be liquid permeable, it is desired that it provides a relatively cloth-like texture to the wearer.

The inner layer of the outer cover 40 is preferably liquid impermeable and vapor permeable. The inner layer is desirably manufactured from a thin plastic film, although other flexible liquid impermeable materials may also be used. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. One example of a suitable microporous film includes a core layer and one or two adjacent thin skin layers. The core layer can be made from a mixture of one or more thermoplastic polymers and a particulate filler, such as calcium carbonate, such that voids are formed around the filler particles when the film is stretched. The skin layers are formed from a polymer blend and either break up during the stretching process or are suitably composed of known high water vapor permeable polymers. Another example of a suitable microporous film includes nonwoven laminates having a microporous film layer.

The liquid permeable bodyside liner 42 is illustrated as overlying the outer cover 40 and absorbent core 44 (FIG. 3), and may but need not have the same dimensions as the outer cover 40. The bodyside liner 42 is desirably compliant, soft feeling, and non-irritating to the child's skin. Further, the bodyside liner 42 can be less hydrophilic than the absorbent core 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent core include materials that are generally not elastomeric.

The absorbent core 44 (FIG. 3) is positioned between the bodyside liner 42 and the hydrophobic foam dampness-inhibiting layer 41. The absorbent core 44 can be any structure which is generally compressible, conformable, non-irritating to the child's skin, and capable of absorbing and retaining liquids and certain body wastes. The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent core 44 to better contain and absorb body exudates. The concentration of the superabsorbent particles can also vary through the thickness of the absorbent core 44. Alternatively, the absorbent core 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent core 44 is substantially rectangular in shape, and includes a blend of wood pulp fluff and superabsorbent material. One preferred type of fluff is identified with the trade designation CR-1654, available from U.S. Alliance Pulp Mills, Coosa, Ala., U.S.A., and is a bleached, highly absorbent sulfate wood pulp containing primarily soft wood fibers. As a general rule, the superabsorbent material is present in the absorbent core 44 in an amount of from about 5 to about 90 weight percent based on total weight of the absorbent core. The absorbent core 44 suitably has a density within the range of about 0.10 to about 0.35 grams per cubic centimeter. The absorbent core 44 may or may not be wrapped or encompassed by a suitable tissue wrap that maintains the integrity and/or shape of the absorbent core.

The hydrophobic foam dampness-inhibiting layer 41 is positioned directly beneath the outer cover 40, between the absorbent core 44 and the outer cover 40. The foam layer 41, due to its three-dimensional structure, maintains an air space within the foam layer 41. The air space, partially encapsulated in foam layer interstices, insulates the outer cover 40 from the absorbent core 44 and slows heat transfer from a person's fingers to the absorbent garment 20, causing the outer surface of the outer cover 40 to feel less clammy and cold. The air space, in combination with the hydrophobic foam dampness-inhibiting material, provides a resilient, soft, springy surface to the fingers, giving an aesthetic improvement over feeling just the wet absorbent core 44 beneath the outer cover 40 in the absence of the foam layer. In theory, the air within the foam layer also provides pathways for side diffusion and convection, speeding the removal of moisture from the absorbent garment 20, especially moisture near the wearer's skin. The departure of moisture contributes to reduced, thereby improved, skin hydration.

The hydrophobic foam dampness-inhibiting layer 41 acts to separate the wet superabsorbent material of the absorbent core 44 from the inside surface of the outer cover 40, thereby allowing a large surface area in which water molecules can migrate across the air/superabsorbent material interface, since the majority of the outer cover 40 micropores are not blocked by the superabsorbent material. The foam dampness-inhibiting layer 41 is therefore permeable enough to not occlude moisture from leaving the absorbent garment 20 in any appreciable amount. In order to allow sufficient insulation and dampness inhibition between the wet superabsorbent material of the absorbent core 44 and the inside surface of the outer cover 40, the thickness of the foam dampness-inhibiting layer 41 is in a range of 0.1 mm to 10 mm, more suitably in a range of 0.3 mm to 7 mm.

The hydrophobic foam dampness-inhibiting layer 41 suitably covers the same amount of surface area as the absorbent core 44, or less. Suitable materials for the hydrophobic foam dampness-inhibiting layer 41 include, but are not limited to, one or more of the following: polyethylene foams, polypropylene foams, hydrophobic polyurethane foams, foams with hydrophobic treatment, coextruded foams, bicomponent foams, multicomponent hydrophobic foams, hybrids of foam and other fibers, slit foams, apertured foams, slit and stretched foams, foam netting, three-dimensional formed foam, three-dimensional formed foam netting, corrugated foam, open cell foam, hybrid foam, foamed fibers, foamed bicomponent fibers, and nonwoven webs containing any of the listed foam substances. Other suitable materials for, or in addition to, the foam spacer layer 41 include foam-coated substrates, such as foam-coated nonwoven webs or foam-coated tissues or other foam-coated lightweight materials. In one embodiment of the invention, the outer cover 40 includes a foam-coated substrate.

Figure 4:
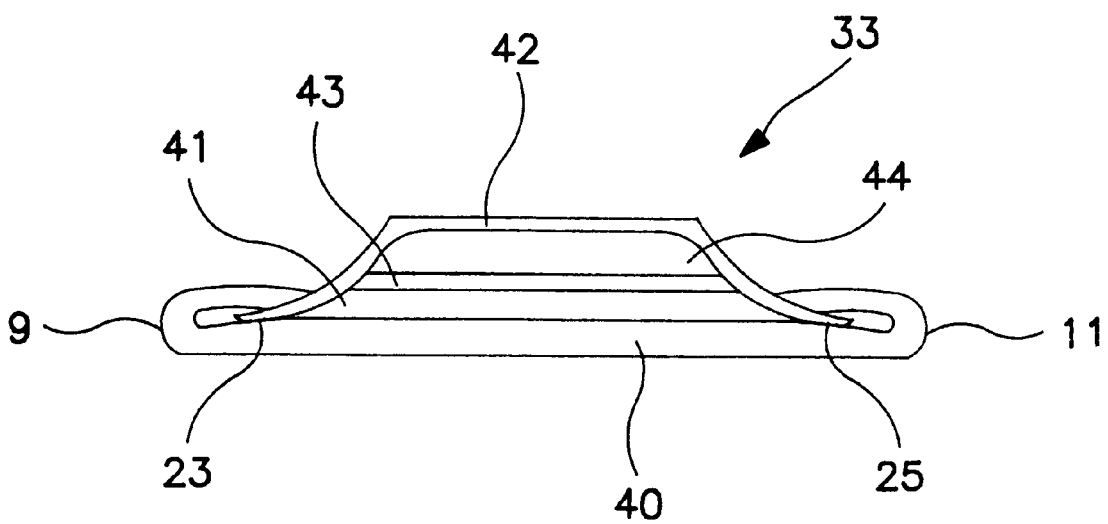
FIG. 4 is an expanded sectional view of one embodiment of the foam dampness-inhibiting layer used in the absorbent article of the invention.

In another embodiment of the invention, shown in FIG. 4, a thin layer 43 of absorbent material is inserted between the absorbent core 44 and the hydrophobic foam dampness-inhibiting layer 41. The term "thin layer" refers to a layer of material having a thickness less than 0.5 mm, more suitably less than 0.1 mm. The surface of the thin layer 43 adjacent the hydrophobic foam dampness-inhibiting layer 41 is made to be nonwettable. The foam dampness-inhibiting layer 41 need not be hydrophobic in this case. The surface of the thin layer 43 can be made nonwettable by treating the absorbent with a fluorocarbon, silicone, or any other suitable nonwetting solution. The nonwetting solution can be applied by any suitable means, such as spraying, brush coating, or the like.

The surface can also be made from a nonwettable pulp which could be separate or part of the absorbent structure and/or hydrophobic microfibers can be sprayed into the pulp to make a nonwettable coform layer. Furthermore, the entire thickness of the thin layer 43 can be made nonwettable. The layer 43 itself can include any of a number of suitable materials including nonwoven webs, tissue, pulp and paper.

The absorbent chassis 32 can also incorporate other materials that are designed primarily to receive, temporarily store, and/or transport liquid along the mutually facing surface with the absorbent core 44, thereby maximizing the absorbent capacity of the absorbent core. One suitable material is referred to as a surge layer (not shown) and includes a material having a basis weight of about 50 grams per square meter, and including a through-air-bonded-carded web of a homogenous blend of 60 percent 3 denier bicomponent fiber including a polyester core/polyethylene sheath, commercially available from BASF Corporation, and 40 percent 6 denier polyester fiber, commercially available from Hoechst Celanese Corporation, in Portsmouth, Va., U.S.A.

As noted previously, the illustrated training pant 20 has front and back side panels 34 and 134 disposed on each side of the absorbent chassis 32 (FIGS. 1 and 2). These transversely opposed front side panels 34 and transversely opposed back side panels 134 can be permanently bonded to the composite structure 33 of the absorbent chassis 32 in the respective front and back waist regions 22 and 24, and are releasably attached to one another by a fastening system 80. More particularly, as shown best in FIG. 2, the front side panels 34 can be permanently bonded to and extend transversely beyond the linear side edges 47 of the composite structure 33 in the front waist region 22 along attachment lines 66, and the back side panels 134 can be permanently bonded to and extend transversely beyond the linear side edges of the composite structure in the back waist region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover or the bodyside liner.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68, as is best shown in FIG. 2.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material (See FIGS. 1 and 2). Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between the distal edge 68 and the respective front or back center panel 35 or 135. In the illustrated embodiment in FIG. 2, the interior portions 78 are disposed between the distal edges 68 and the side edges 47 of the rectangular composite structure 33. The elastic material of the side panels 34 can be disposed in the interior portions 78 to render the side panels elastomeric in a direction generally parallel to the transverse axis 49. Most desirably, each side panel 34 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68 and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

The absorbent chassis 32 and the fastening system 80 together define a refastenable pant having a waist opening 50 and a pair of leg openings 52 (FIG. 1). When the fastening system is engaged, it can be appreciated that the refastenable pant includes a pair of elastomeric front side panels 34 extending from the waist opening to each leg opening, a pair of elastomeric back side panels 134 extending from the waist opening to each leg opening, a pair of refastenable seams 88 (FIG. 1) extending from the waist opening to each leg opening and positioned between the elastomeric front and back side panels, an elastomeric front waistband 54 disposed in the front waist region 22 and positioned between the pair of elastomeric front side panels, an elastomeric back waistband 56 disposed in the back waist region 24 and positioned between the pair of elastomeric back side panels, and at least a pair of elastomeric leg members 58 which partially encircle each leg opening 52. More preferably, more than one elastomeric leg member 58 partially or fully encircles each leg opening 52. Each elastomeric leg member 58 extends from adjacent an elastomeric front side panel 34 in the front waist region 22 to adjacent an elastomeric back side panel 134 in the back waist region 24. Alternatively, instead of refastenable seams 88, the absorbent garment 20 can have bonded side seams (not shown).

As described herein, the various components of the training pant 20 can be integrally assembled together employing various types of suitable attachment means, such as adhesive, sonic and thermal bonds or combinations thereof. The resulting product is an absorbent garment having a breathable outer cover material and reduced perceived outer cover dampness.

EXAMPLES

For the following examples, five Huggies® diapers were modified by changing the outer covers and the spacer layers, and one Huggies® diaper was tested without any modifications to the outer cover or spacer layer. The six samples were tested and compared in terms of humidity, temperature, and dampness effects inside each diaper. The samples were: SAMPLE 1, a standard Huggies® diaper, which has a nominal 25,000 WVTR outer cover and a commercial 0.8 osy spunbond-meltblown-spunbond (SMS) spacer layer; SAMPLE 2 which has a nominal 25,000 WVTR outer cover and a closed cell polyurethane foam ("CL. CELL") spacer layer with a 0.25 inch (0.64 cm) bulk, the closed cell foam layered to achieve such bulk; SAMPLE 3 which has a nominal 1,500 WVTR low breathable film outer cover and no spacer layer; SAMPLE 4 which has a nominal 25,000 WVTR outer cover and an open cell polyurethane foam ("OP. CELL") spacer layer with a 0.25 inch (0.64 cm) bulk; SAMPLE 5 which has a nominal 25,000 WVTR outer cover and a through-air bonded carded web spacer layer of polyester and bi-component fibers with a 0.25 inch (0.64 cm) bulk; and SAMPLE 6 which has a nominal 25,000 WVTR outer cover and no spacer layer. The nominal 25,000 WVTR outer cover film is a metallocene catalyzed polyethylene, calcium carbonate filled, machine direction stretched film. The nominal 1,500 WVTR low breathable outer cover film is a Ziegler-Natta polyethylene, calcium carbonate filled, machine direction stretched film.

A heated torso bench test was performed on each of the sample diapers. Each sample diaper was filled with 180 mls of saline using three 60 ml insults 15 minutes apart. The insult zone was 2 inches (5 centimeters) towards the waist from the center of the absorbent core. Each sample diaper was then placed on a heated torso heated to body temperature to create a simulated use-like environment both inside and outside a saturated diaper. Each diaper was left on the torso in a controlled temperature and humidity environment of 70 degrees Fahrenheit (21 degrees Celsius), 50% humidity for two hours to allow the sample diapers to start the evaporation process. A temperature and humidity probe was placed in the product at the insult point for at least 30 minutes to equilibrate the inside diaper environment. Room temperature and room humidity were treated as baselines and the measured temperature and measured humidity were the amount over room temperature and room humidity.

After two hours in the controlled temperature and humidity environment, the temperature and humidity probes were used to measure the internal and external sample diaper environments. The temperature on the outer cover was measured with an infrared gun at the midpoint of the absorbent core and at the insult point 2 inches (5 centimeters) forward of the midpoint. The "front mid" temperature was the average of these two temperatures. The temperature on the outer cover was also measured in the back of the products at the midpoints of the left and right butt cheeks. The "rear" average temperature was the average of these two temperatures.

Figure 11:
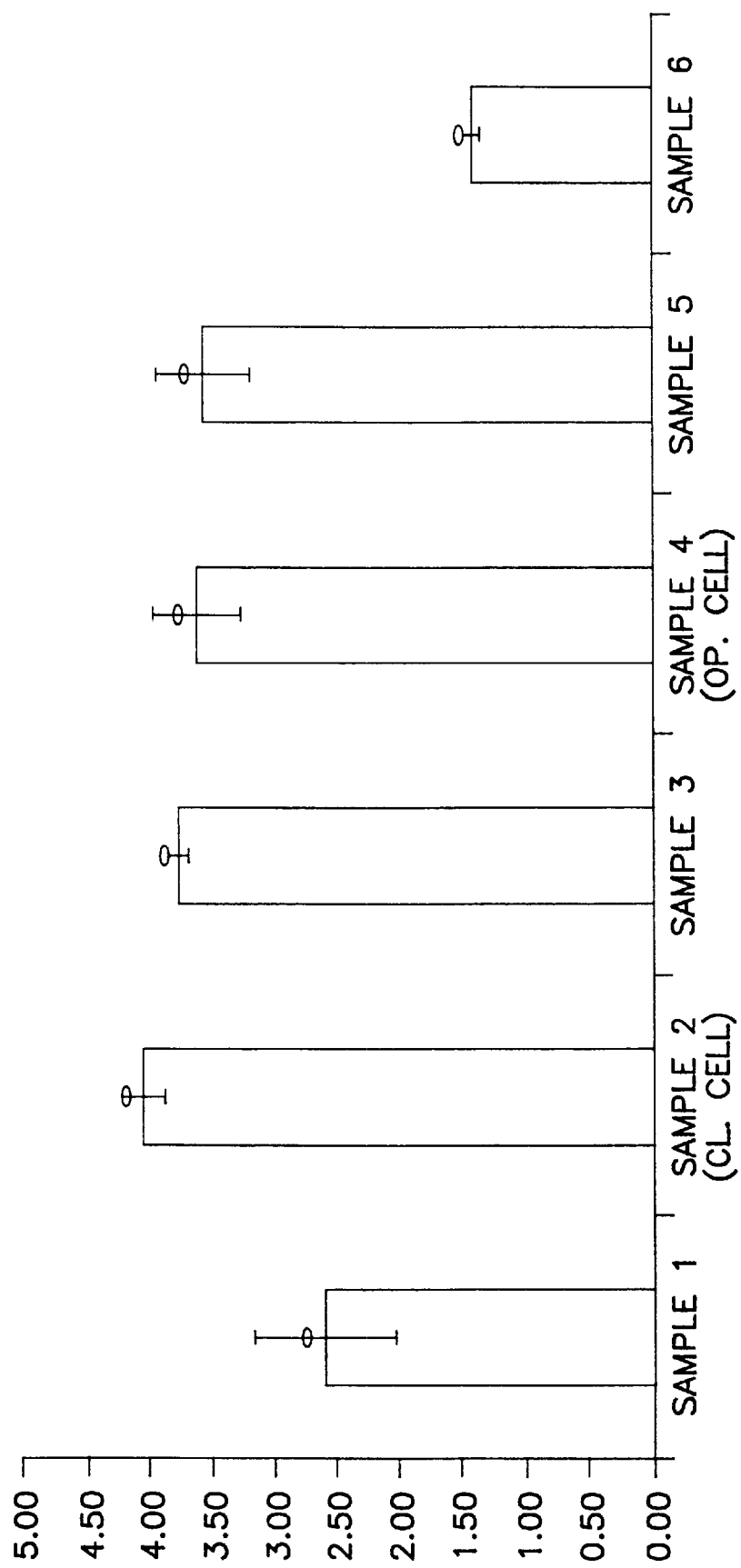
FIG. 11 is a chart showing warmth measurements of the front portions of six different sample diapers constructed of 6 different materials.
Figure 12:
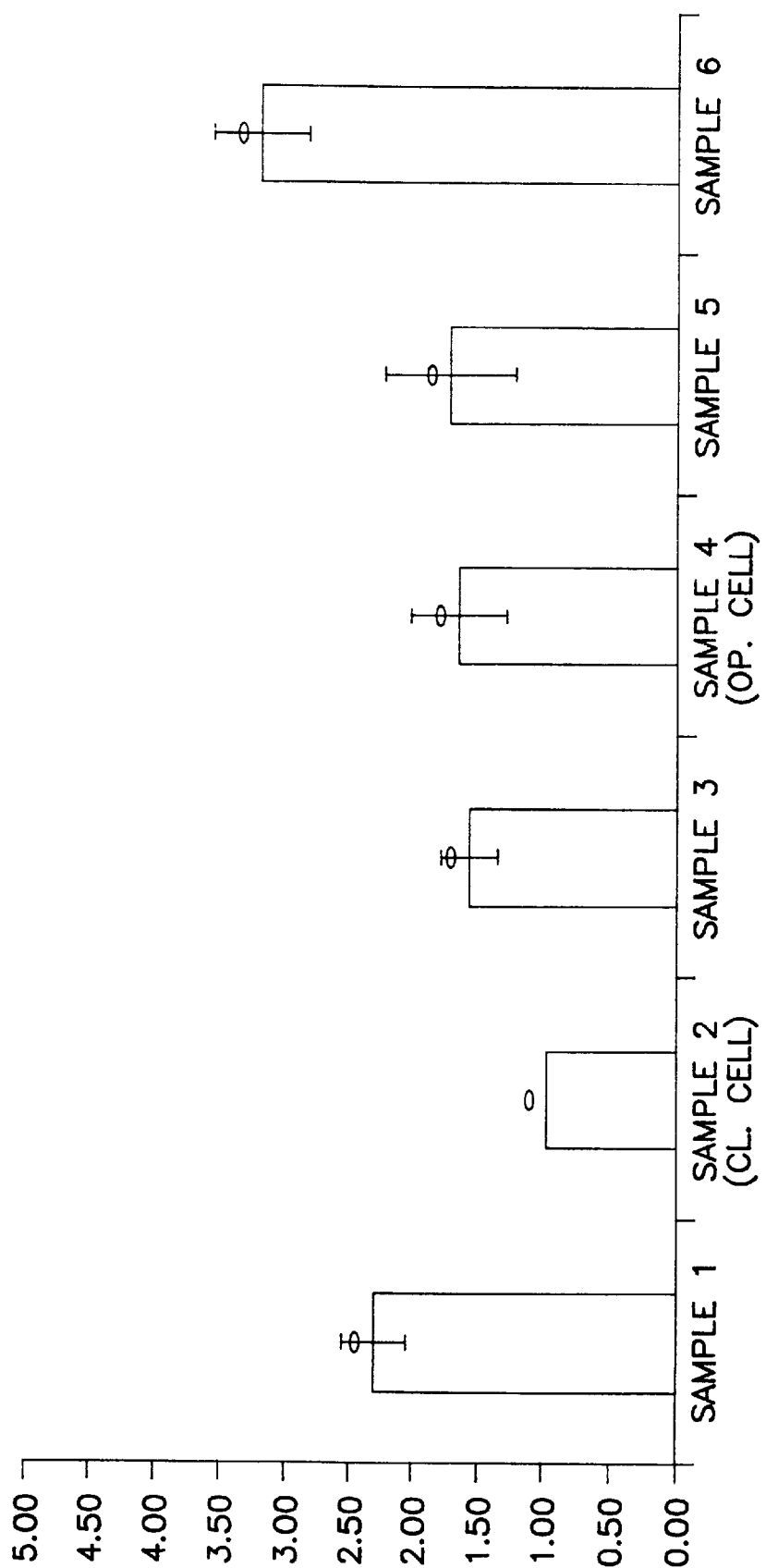
FIG. 12 is a chart showing dampness measurements of the front portions of six different sample diapers constructed of 6 different materials.

A hand dampness perception test and a warmth perception test were also performed. A comparison of the outer cover dampness and warmth perception was carried out using control codes (SAMPLES 3 and 6) and comparing these to the spacer codes (SAMPLES 1, 2, 4 and 5). As indicated in FIG. 11, warmth was measured on a scale of 1 to 5, 1 being the coldest possible measurement and 5 being the warmest possible measurement. Similarly, as indicated in FIG. 12, dampness was measured on a scale of 1 to 5, 1 being the driest possible measurement and 5 being the dampest possible measurement. The first standard code, SAMPLE 3, having a low-breathable outer cover and no spacer, was perceived as warm (rated between a value of 3 and 4, FIG. 11) and relatively dry (below a value 2, FIG. 12). The second standard code, SAMPLE 6, having a high-breathable outer cover and no spacer, was perceived as cold (rated between a value of 1 and 2, FIG. 11) and very damp (above 3, FIG. 12).

TEST 1

Figure 5:
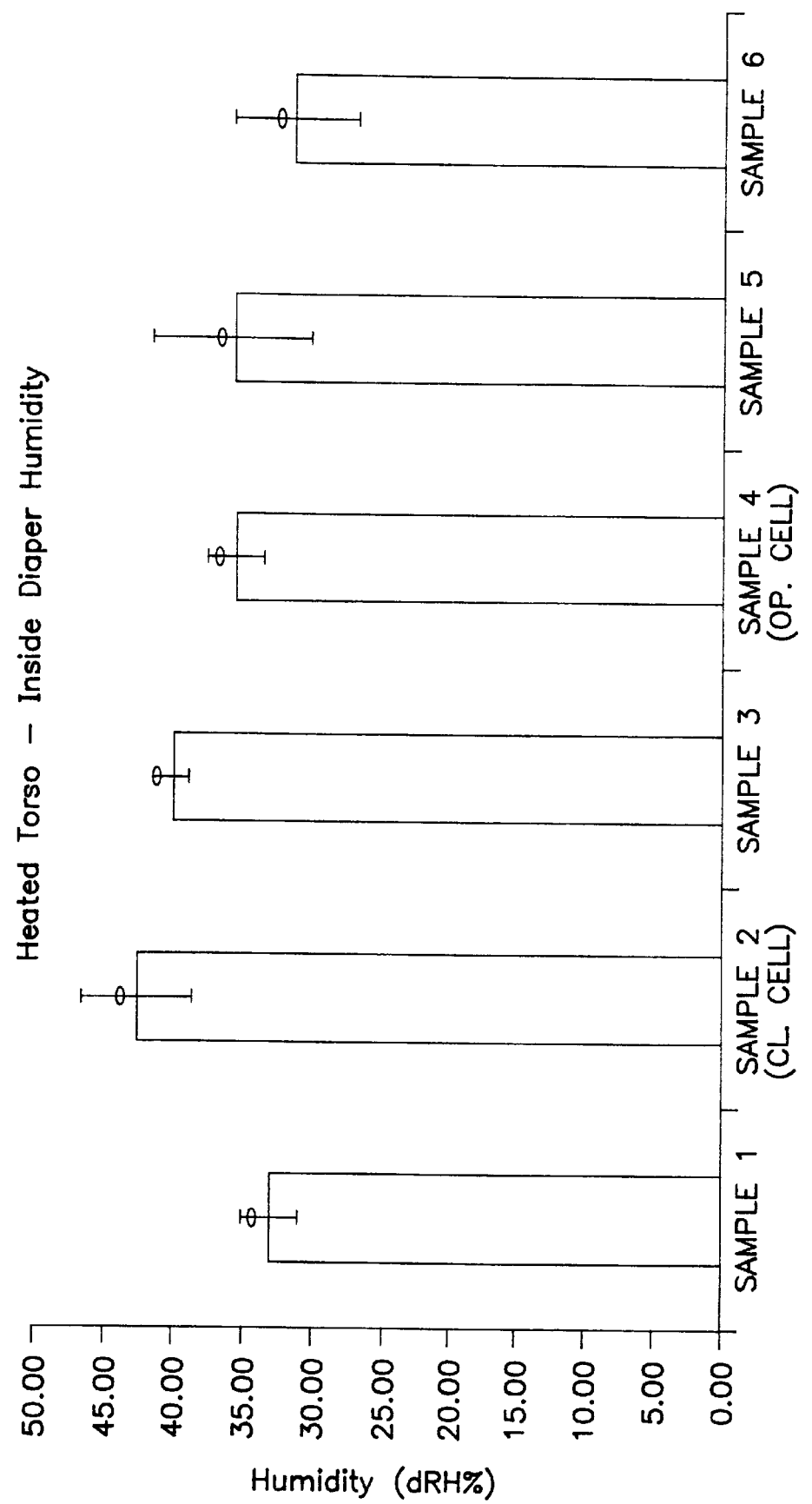
FIG. 5 is a chart showing inside diaper humidity of six different sample diapers constructed of 6 different materials.

Humidity inside each sample diaper was measured and compared, as described above. The results are shown in FIG. 5. As can be seen in FIG. 5, the closed cell foam (SAMPLE 2) negates the effect of a breathable outer cover by not allowing fluid to evaporate out of the diaper. Similarly, the low-breathable outer cover (SAMPLE 3) also inhibits fluid evaporation out of the diaper. In contrast, the open cell foam (SAMPLE 4) allows the breathable outer cover to function, thereby allowing the diaper to breathe.

TEST 2

Figure 6:
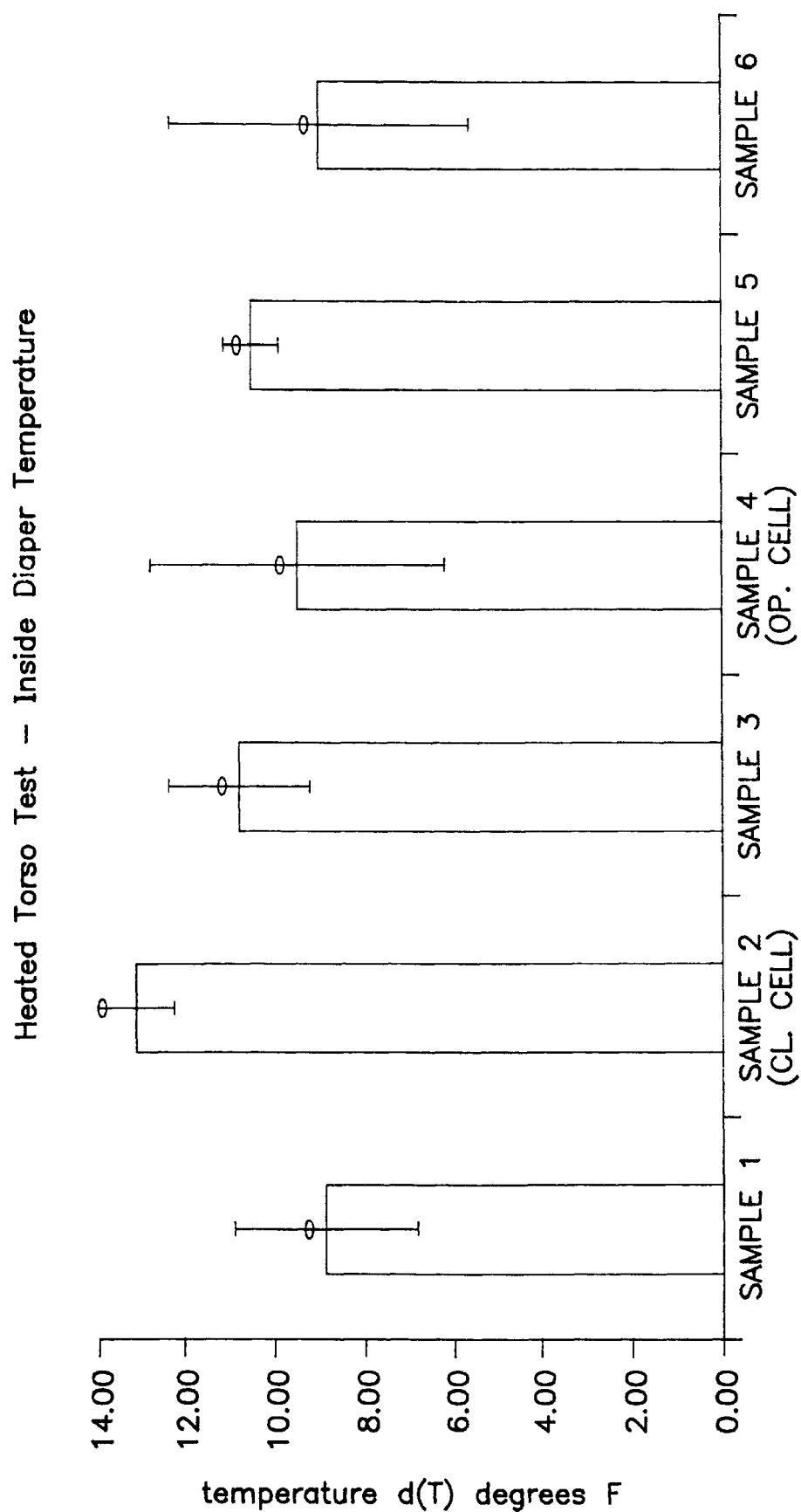
FIG. 6 is a chart showing inside diaper temperatures of six different sample diapers constructed of 6 different materials.

Temperature inside each sample diaper was measured and compared, as described above. The results are shown in FIG. 6. As can be seen in FIG. 6, the closed cell foam (SAMPLE 2) maintains a higher temperature inside the diaper than the open cell foam (SAMPLE 4) because there is little evaporative cooling in SAMPLE 2.

TEST 3

Figure 7:
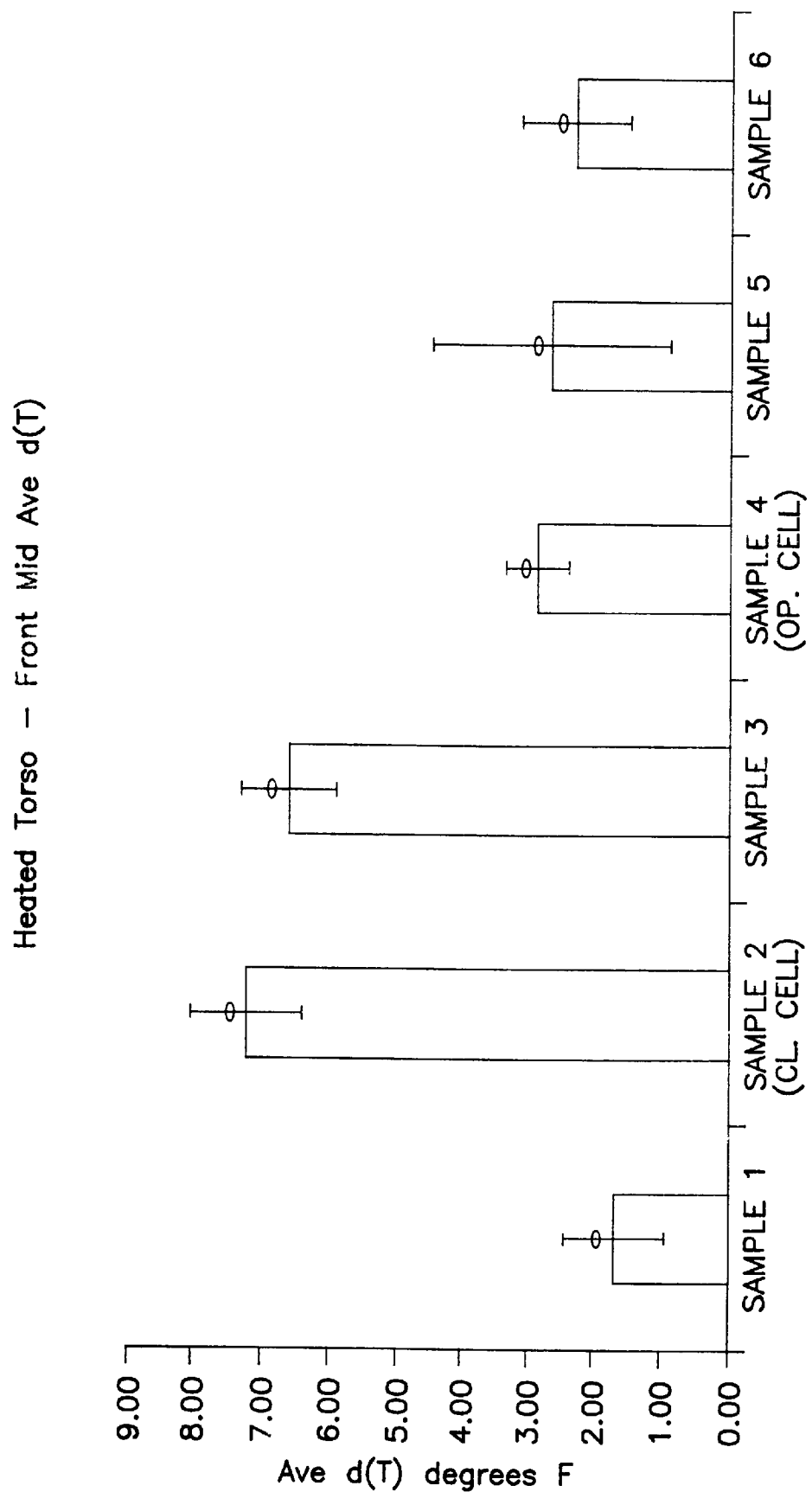
FIG. 7 is a chart showing temperature differentials of the front and middle portions of six different sample diapers constructed of 6 different materials.

Average differential temperature in the front and middle portion of each sample diaper was measured and compared, as described above. The results are shown in FIG. 7. As can be seen in FIG. 7, the closed cell foam sample diaper (SAMPLE 2) and the low-breathable sample diaper (SAMPLE 3) experience much higher internal temperatures than the open cell foam sample diaper (SAMPLE 4) because there is little evaporative cooling in SAMPLES 2 and 3.

TEST 4

Figure 8:
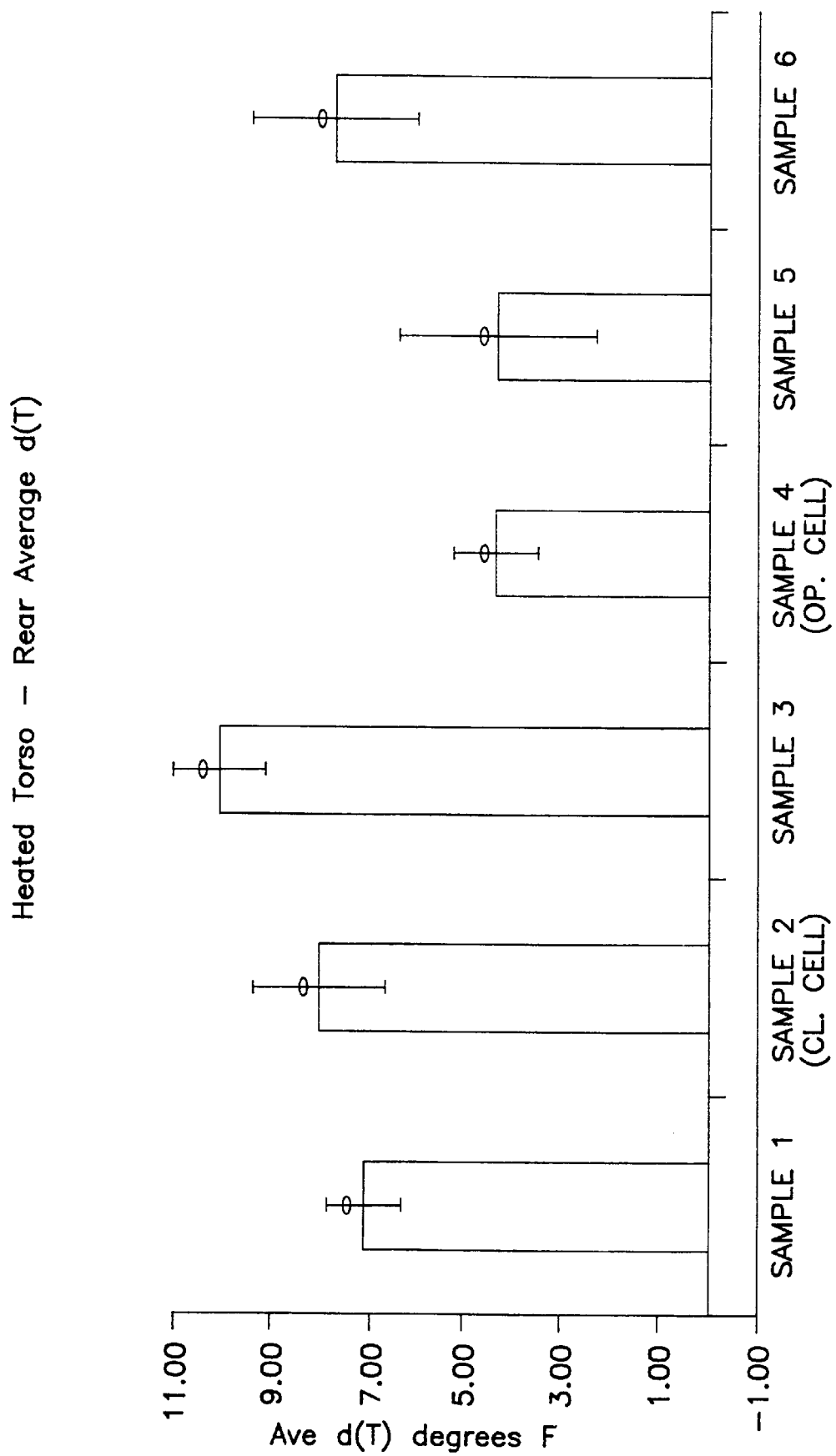
FIG. 8 is a chart showing temperature differentials of the rear portion of six different sample diapers constructed of 6 different materials.

Average differential temperature in the rear portion of each sample diaper was measured and compared, as described above. The results are shown in FIG. 8. As can be seen in FIG. 8, the closed cell foam sample diaper (SAMPLE 2) and the low-breathable sample diaper (SAMPLE 3) experience much higher internal temperatures than the open cell foam sample diaper (SAMPLE 4) because there is little evaporative cooling in SAMPLES 2 and 3.

TEST 5

Figure 9:
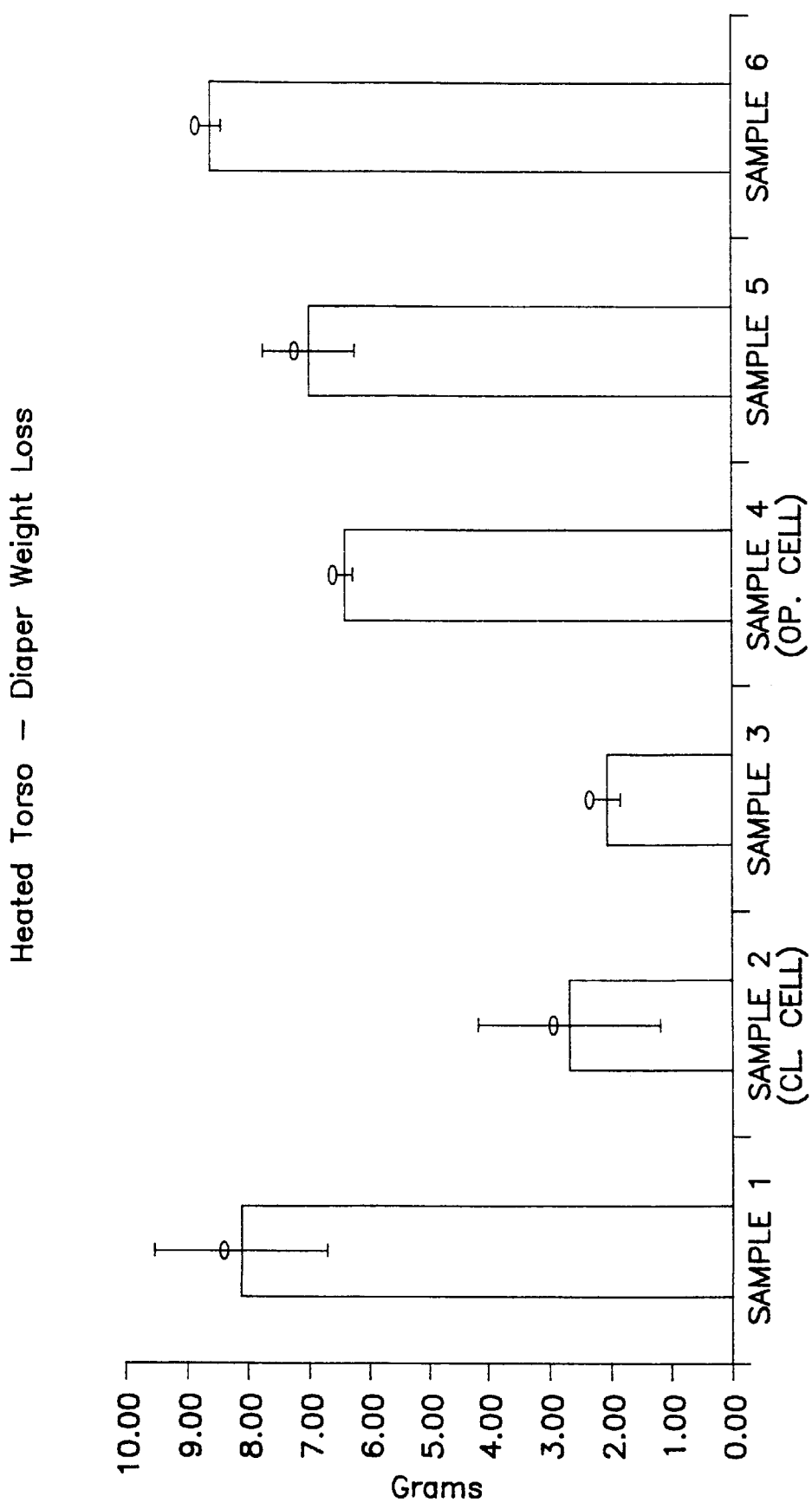
FIG. 9 is a chart showing weight loss of six different sample diapers constructed of 6 different materials.

Weight loss of each sample diaper was measured and compared, as described above. The weight loss corresponds to the amount of moisture that escapes from the diaper. The results are shown in FIG. 9. As can be seen in FIG. 9, the closed cell foam sample diaper (SAMPLE 2) experiences less weight loss than the open cell foam sample diaper (SAMPLE 4) because the closed cell foam (SAMPLE 2) appears to occlude the high-breathable outer cover by not allowing fluid to evaporate out of the diaper. Similarly, the low-breathable outer cover (SAMPLE 3) also inhibits fluid evaporation out of the diaper and experiences less weight loss than the open cell foam sample diaper (SAMPLE 4).

TEST 6

Figure 10:
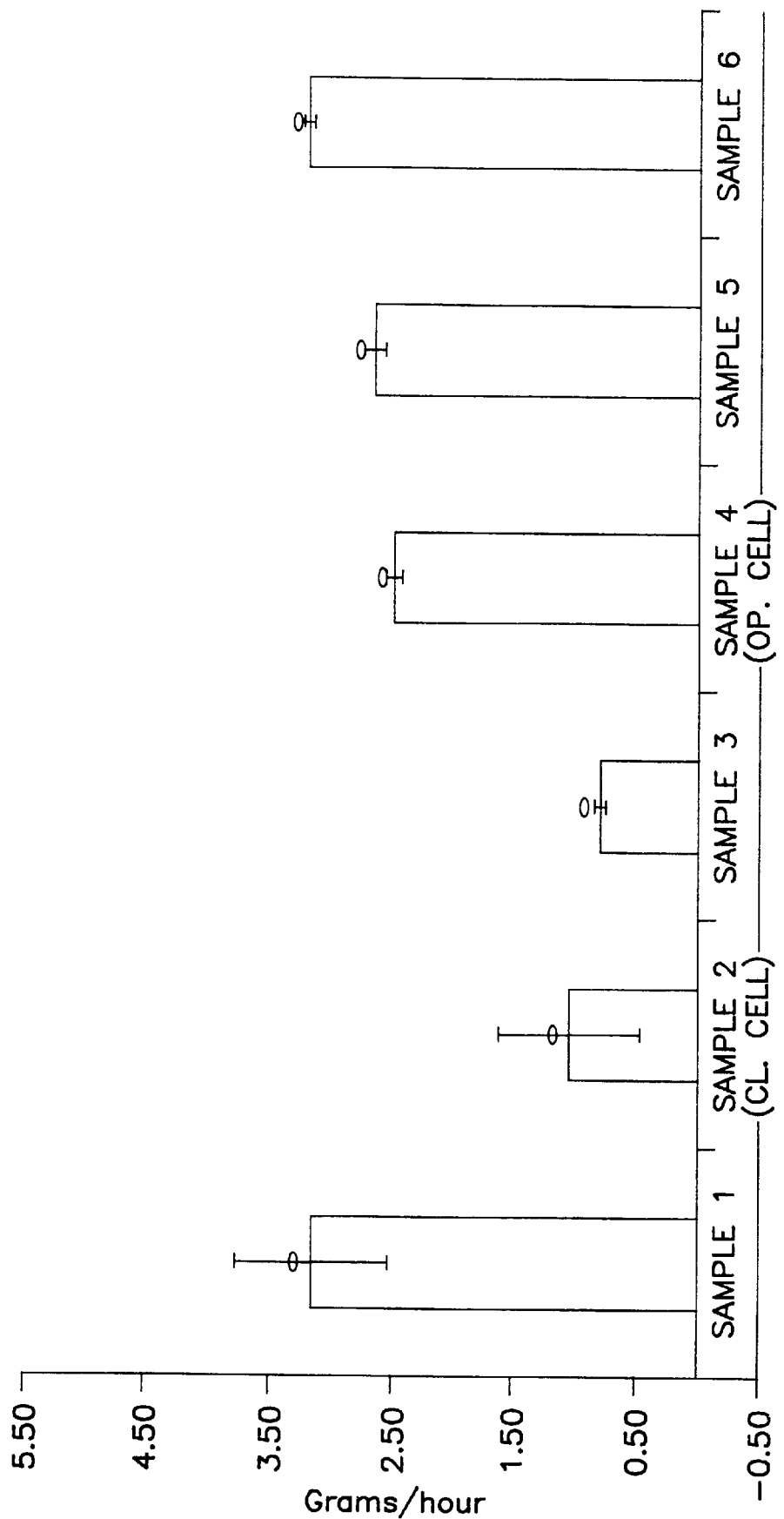
FIG. 10 is a chart showing evaporation rates of six different sample diapers constructed of 6 different materials.

Evaporation rates occurring in each sample diaper were measured and compared, as described above. The results are shown in FIG. 10. As can be seen in FIG. 10, evaporation occurs much more quickly in the open cell foam sample diaper (SAMPLE 4) than in either the closed cell foam sample diaper (SAMPLE 2) or the low-breathable outer cover sample diaper (SAMPLE 3). The closed cell foam (SAMPLE 2) appears to occlude the high-breathable outer cover by not allowing fluid to evaporate out of the diaper. Similarly, the low-breathable outer cover (SAMPLE 3) also inhibits fluid evaporation out of the diaper. Furthermore, internal humidity is lower in the open cell foam sample (SAMPLE 4) than in either the closed cell foam sample (SAMPLE 2) or the low-breathable outer cover sample (SAMPLE 3) (FIG. 5), thus providing skin health benefits, i.e. reduced skin moisture, in the open cell foam sample (SAMPLE 4).

TEST 7

The warmth of each sample diaper was measured in the above described test procedure. The results are shown in FIG. 11. As can be seen in FIG. 11, the warmth of the closed cell foam sample diaper (SAMPLE 2) and the warmth of the open cell foam sample diaper (SAMPLE 4) were very close, with the closed cell foam sample diaper measuring slightly warmer than the open cell foam sample diaper. This occurs eve though the surface temperature of SAMPLE 4 was considerably less than the surface temperature of SAMPLE 6 (TEST 3, FIG. 7). However, the open cell foam sample (SAMPLE 4) provides skin health benefits not found in the closed cell foam sample (SAMPLE 2) due to lower internal humidity in the open cell foam sample (SAMPLE 4) (FIG. 5).

TEST 8

Dampness in the front portion of each sample diaper was measured and compared, as described above. The results are shown in FIG. 12. As can be seen in FIG. 12, the open cell foam sample diaper (SAMPLE 4) was drier than both the non-modified Huggies® diaper (SAMPLE 1) and the high-breathable outer cover sample diaper with no spacer (SAMPLE 6).

As shown in TESTS 1–8, and corresponding FIGS. 5–12, the closed cell foam (SAMPLE 2) negates the effect of a breathable outer cover by not allowing fluid to evaporate out of the diaper. The open cell foam (SAMPLE 4) allows the breathable outer cover to function, as does the through-air bonded carded web spacer (SAMPLE 5). Both the open cell foam and the through-air bonded carded web spacer allow the diapers to breathe while maintaining a perception of warmth and dryness on the outer cover. Both of these sample diapers (SAMPLES 4 and 5) were perceived as much warmer and drier than the sample with the SMS spacer layer (SAMPLE 1). Furthermore, the open cell foam spacer may be advantageous over the through-air bonded carded web spacer because the open cell foam is much less wettable and less permeable, thereby staying drier in a dynamic use situation than the through-air bonded carded web spacer and maintaining warmth and dryness perceptions better than the through-air bonded carded web spacer.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

Test Procedure For Water Vapor Transmission Rate (WVTR)

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:
WVTR: The calculation of the WVTR uses the formula:

$$WVTR = F p_{sat}(T) RH / A p_{sat}(T)(1-RH))$$

where:
F=The flow of water vapor in cc/min.,
$p_{sat}(T)$=The density of water in saturated air at temperature T,
RH=The relative humidity at specified locations in the cell,
A=The cross sectional area of the cell, and,
$p_{sat}(T)$=The saturation vapor pressure of water vapor at temperature T.

We claim:
1. An absorbent article, comprising:
a liquid-permeable bodyside liner;
an absorbent core layer;
a breathable outer cover; and
a dampness-inhibiting layer positioned between the absorbent core layer and the breathable outer cover;
wherein the dampness-inhibiting layer comprises a hydrophobic foam-coated substrate.

2. The absorbent article of claim 1 wherein the foam coating comprises a material selected from the group consisting of: polyethylene foams, polypropylene foams, hydrophobic polyurethane foams, foams with hydrophobic treatment, coextruded foams, bicomponent foams, multi-component hydrophobic foams, hybrids of foam and other fibers, slit foams, apertured foams, slit and stretched foams, foam netting, three-dimensional formed foam, three-dimensional formed foam netting, corrugated foam, open cell foam, hybrid foam, foamed fibers, foamed bicomponent fibers, and combinations thereof.

3. The absorbent article of claim 1, wherein the substrate comprises a nonwoven web.

4. The absorbent article of claim 1, wherein the substrate comprises tissue.

5. The absorbent article of claim 1 wherein the dampness-inhibiting layer has a thickness in a range of 0.1 mm to 10 mm.

6. The absorbent article of claim 1 wherein the dampness-inhibiting layer has a thickness in a range of 0.3 mm to 7 mm.

7. The absorbent article of claim 1 wherein the foam-coated substrate covers one surface of the absorbent core layer.

8. The absorbent article of claim 1, further comprising a second layer of material positioned between the absorbent core and the dampness-inhibiting layer, wherein a surface of the second layer of material is nonwettable.

9. The absorbent article of claim 8, wherein the nonwettable surface of the second layer of material comprises a fluorocarbon coating.

10. The absorbent article of claim 8, wherein the nonwettable surface of the second layer of material comprises a silicone coating.

11. The absorbent article of claim 8, wherein the nonwettable surface of the second layer of material comprises a nonwettable pulp.

12. The absorbent article of claim 8, wherein the nonwettable surface of the second layer of material comprises hydrophobic microfibers.

13. An absorbent article, comprising:
a liquid-permeable bodyside liner;
an absorbent core layer;
a breathable outer cover; and
a dampness-inhibiting hydrophobic foam layer positioned between the absorbent core layer and the breathable outer cover;
wherein the breathable outer cover layer comprises a hydrophobic foam-coated substrate.

14. The absorbent article of claim 13 wherein the foam layer comprises a material selected from the group consisting of: polyethylene foams, polypropylene foams, hydrophobic polyurethane foams, foams with hydrophobic treatment, coextruded foams, bicomponent foams, multicomponent hydrophobic foams, hybrids of foam and other fibers, slit foams, apertured foams, slit and stretched foams, foam netting, three-dimensional formed foam, three-dimensional formed foam netting, corrugated foam, open cell foam, hybrid foam, foamed fibers, foamed bicomponent fibers, and combinations thereof.

15. The absorbent article of claim 13 wherein the foam coating comprises a material selected from the group consisting of: polyethylene foams, polypropylene foams, hydrophobic polyurethane foams, foams with hydrophobic treatment, coextruded foams, bicomponent foams, multicomponent hydrophobic foams, hybrids of foam and other fibers, slit foams, apertured foams, slit and stretched foams, foam netting, three-dimensional formed foam, three-dimensional formed foam netting, corrugated foam, open cell foam, hybrid foam, foamed fibers, foamed bicomponent fibers, and combinations thereof.

16. An absorbent article, comprising:
   a liquid-permeable bodyside liner;
   an absorbent core layer;
   a breathable outer cover;
   a dampness-inhibiting layer, comprising a hydrophobic foam-coated substrate, positioned between the absorbent core layer and the breathable outer cover; and
   a second layer of material positioned between the absorbent core layer and the dampness-inhibiting layer, wherein a surface of the second layer of material is nonwettable.

17. The absorbent article of claim 16, wherein the nonwettable surface of the second layer of material comprises a fluorocarbon coating.

18. The absorbent article of claim 16, wherein the nonwettable surface of the second layer of material comprises a silicone coating.

19. The absorbent article of claim 16, wherein the nonwettable surface of the second layer of material comprises a nonwettable pulp.

20. The absorbent article of claim 16, wherein the nonwettable surface of the second layer of material comprises hydrophobic microfibers.

21. The absorbent article of claim 16, wherein the second layer of material comprises an absorbent material.

* * * * *

UNITED STATES PATENT AND TRADEMARK OFFICE
CERTIFICATE OF CORRECTION

PATENT NO.   : 6,600,086 B1
DATED        : July 29, 2003
INVENTOR(S)  : Tamara Lee Mace et al.

It is certified that error appears in the above-identified patent and that said Letters Patent is hereby corrected as shown below:

Column 17,
Line 66, replace the existing equation with the following equation:
-- $WVTR = F\rho_{sat}(T)RH/A\rho_{sat}(T)(1-RH)$ --

Column 18,
Line 3, replace "$p_{sat}(T)$" with -- $\rho_{sat}(T)$ --

Signed and Sealed this

Twelfth Day of October, 2004

JON W. DUDAS
*Director of the United States Patent and Trademark Office*